United States Patent [19]

Abou-Gharbia et al.

[11] Patent Number: 4,638,008
[45] Date of Patent: Jan. 20, 1987

[54] ANTIARRHYTHMIC AGENTS

[75] Inventors: Magid A. Abou-Gharbia, Wilmington, Del.; Meier E. Freed; Thomas J. Colatsky, both of Paoli, Pa.

[73] Assignee: American Home Products Corporation, New York, N.Y.

[21] Appl. No.: 740,651

[22] Filed: Jun. 3, 1985

Related U.S. Application Data

[62] Division of Ser. No. 684,211, Dec. 20, 1984, Pat. No. 4,546,193.

[51] Int. Cl.$^4$ ............................................. A61K 31/40
[52] U.S. Cl. .................................... 514/411; 514/821
[58] Field of Search ................................ 514/411, 821

[56] References Cited

U.S. PATENT DOCUMENTS 3,282,942  11/1966  Rice et al. ........................... 260/268

OTHER PUBLICATIONS

Rice et al., J. Med. Chem., 7, 313 (1964).
Derwent 36802 T, 1970.
Derwent 22763 T, 1968.
Derwent 10718 W, 1971.

Primary Examiner—Frederick E. Waddell
Attorney, Agent, or Firm—Richard K. Jackson

[57] ABSTRACT

This invention provides a group of antiarrythmic agents of the formula:

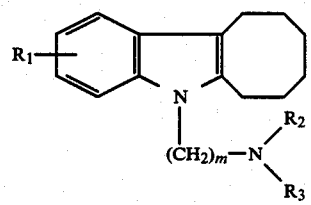

in which
$R_1$ is $-CO_2H$, $-CO_2(CH_2)_n-NR_4R_5$, $-CONR_6R_7$, $-NHCO_2R_8$ or $-NHCO_2(CH_2)_o-NR_9R_{10}$ where $R_4$ and $R_5$ are H or alkyl of 1 to 6 carbon atoms and n is 1 to 6; $R_6$ and $R_7$ are H or alkyl of 1 to 6 carbon atoms; $R_8$ is alkyl of 1 to 6 carbon atoms; and $R_9$ and $R_{10}$ are alkyl of 2 to 6 carbon atoms and o is 1 to 6;

$R_2$ and $R_3$ are, independently, hydrogen or alkyl of 1 to 6 carbon atoms; and m is one of the integers 1, 2, 3 or 4;

or a pharmaceutically acceptable salt thereof, and a method for their use.

3 Claims, No Drawings

ANTIARRHYTHMIC AGENTS

This is a division of application Ser. No. 684,211 filed Dec. 20, 1984, now U.S. Pat. No. 4,546,193 granted Oct. 8, 1985.

BACKGROUND OF THE INVENTION

Substituted cycloalkano[b]indoles have been previously reported to possess various biological activities including central nervous system activity and antidepressant activity (Rice et al., J. Med. Chem. 7 313 (1964); U.S. Pat. No. 3,282,942), depressant and tranquilizing activity (Derwent 36802T; U.S. Pat. No. 3,663,567 (1970)), antiinflammatory and analgesic activity (Derwent 22763T-B; JA No. 7210707-R (1968)), and antihyperlipidemic activity (Derwent 10718W-06; U.S. Pat. No. 3,862,953 (1971)).

DESCRIPTION OF THE INVENTION

In accordance with this invention there is provided a group of antiarrhythmic agents of the formula:

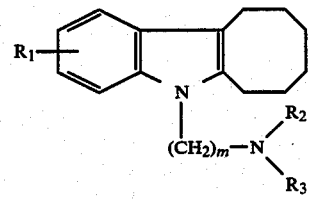

in which $R_1$ is —$CO_2H$, —$CO_2(CH_2)_n$—$NR_4R_5$, —$CONR_6R_7$, —$NHCO_2R_8$ or —$NHCO_2(CH_2)_o$—$NR_9R_{10}$ where $R_4$ and $R_5$ are H or alkyl of 1 to 6 carbon atoms and n is 1 to 6; $R_6$ and $R_7$ are H or alkyl of 1 to 6 carbon atoms; $R_8$ is alkyl of 1 to 6 carbon atoms; and $R_9$ and $R_{10}$ are alkyl of 2 to 6 carbon atoms and o is 1 to 6;

$R_2$ and $R_3$ are, independently, hydrogen or alkyl of 1 to 6 carbon atoms; and m is one of the integers 1, 2, 3 or 4;

or a pharmaceutically acceptable salt thereof.

Preferred compounds of this invention are:

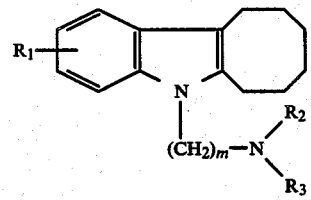

in which $R_1$ is —$NHCO_2R_8$ or —$NHCO_2(CH_2)_o$—$NR_9R_{10}$ where $R_8$ is alkyl of 1 to 6 carbon atoms; $R_9$ and $R_{10}$ are alkyl of 2 to 6 carbon atoms and o is 1 to 6;

$R_2$ and $R_3$ are alkyl of a to 6 carbon atoms; and m is one of the integers 1, 2, 3 or 4;

or a pharmaceutically acceptable salt thereof.

In addition, this invention provides a method for treating cardiac arrhythmias and conditions characterized by coronary arteries vasospasm which comprises orally or parenterally administering to an animal in need thereof an effective amount of a compound of the formula:

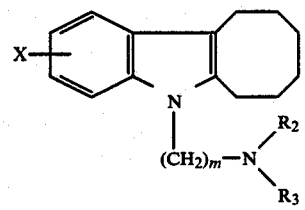

in which

X is —H, —$CO_2H$, —$CO_2(CH_2)_n$—$NR_4R_5$, —$CONR_6R_7$, —$NHCO_2R_8$ or —$NHCO_2(CH_2)_o$—$NR_9R_{10}$ where $R_4$ and $R_5$ are H or alkyl of 1 to 6 carbon atoms and n is 1 to 6; $R_6$ and $R_7$ are H or alkyl of 1 to 6 carbon atoms; $R_8$ is alkyl of 1 to 6 carbon atoms; and $R_9$ and $R_{10}$ are alkyl of 2 to 6 carbon atoms and o is 1 to 6;

$R_2$ and $R_3$ are, independently, hydrogen or alkyl of 1 to 6 carbon atoms; and m is one of the integers 1, 2, 3 or 4;

or a pharmaceutically acceptable salt thereof. This method includes the use of the non-benzo substituted compound iprindole which was also discovered to be a very active antiarrhythmic agent affording inhibition of ventricular fibrilation in all but 11 percent of the standard experimental animals, as discussed, infra.

Those compounds containing a basic amino group are capable of forming acid addition salts. It is intended throughout this specification and claims to embrace the pharmaceutically acceptable salts of such compounds, which salts are conveniently derived from such acids as hydrochloric, hydrobromic, sulfuric, phosphoric, methane sulfonic, nitric, p-toluene sulfonic, acetic, citric, maleic, succinic acid and the like. In addition, the compounds in their free carboxylic acid form are converted by standard techniques well-known to the chemist into alkali metal (sodium or potassium), alkaline earth metal (calcium or magnesium), ammonium or primary, secondary and tertiary alkylamine salts, the latter containing from 1 to 6 carbon atoms in their alkyl moieties.

The compounds of this invention are prepared by reacting a carboxy or nitrophenylhydrazine with cyclooctanone to obtain the hydrazone which upon acidic treatment rearranges to afford the 6,7,8,9,10,11-hexahydro-carboxy or nitro-5H-cyclooct[b]indole. The indole nitrogen atom is alkylated with N,N-dialkylaminoalkyl chloride, the nitro substituent is reduced conventionally to an amino substituent. The carboxy or amino substituents are converted to aminoalkyl esters, amides or carbamates conventionally.

The compounds of this invention demonstrate antiarrhythmic activity when tested in the standard experimental animal in accordance with the following procedure:

Rats weighing between 400–500 gms were anesthetized with 35–40 mg/kg. Na pentobarbital i.p. Rats were close-clipped on the neck and left side prior to cannulation of the jugular vein and tracheotomy. In some experminets, a catheter was introduced into the carotid artery for measurement of arterial blood pressure. Respiration was provided by a Harvard Model 681 respirator at a rate of approximately 55/min and a volume of 4 cc per cycle. The rat was then placed upon its right side and the heart was exposed by making an incision and separating the ribs. 4-0 Silk on taper RB-1 needle was passed under the left anterior descending coronary artery (LAD) at a location just under the tip of the left atrial appendage. The suture was left to be tied upon occlusion. Lead II ECG and cardiotachometer output were recorded on a Beckman R612.

The rat was allowed to stabilize for several minutes before the administration of drug via the cannulated jugular vein. The compounds being tested were suspended in carbowax, with the total dose (up to 15 mg/kg.) volumes kept below 0.20–0.25 ml. Fifteen minutes after dosing, the LAD was occluded by tying the suture. This procedure provokes severe ventricular arrhythmias, terminating in ventricular fibrillation and death in approximately 73 percent of animals given vehicle only. Data were analyzed based on incidence and severity of the occlusion arrhythmia. Relative activity in a series of compounds was further analyzed by assigning a weighted score according to the severity of the arrhythmia observed.

For the purpose of these coronary ligation (C.L.) experiments, the percent ventricular fibrillation, expressed as a percentage of the animals employed, was obtained for purpose of comparison with the control rate of 73 percent in vehicle-treated animals.

Thus, these data establish the compounds of this invention as useful anti-arrhythmic agents. The mechanism by which these compounds produce their anti-arrhythmic result is not known, although the products of Examples 1 and 3 did demonstrate meaningful $Ca^{+2}$ antagonist activity when tested by standard procedures.

Based upon the activity profile elicited by the compounds of this invention in the above-described standard scientifically recognized test model, the compounds are established as anti-arrhythmic agents useful in the treatment and prophylaxis of cardiac arrhythmias and conditions characterized by coronary arteries vasospasm. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established at from 1 to about 15 milligrams, preferably 10 milligrams, per kilogram host body weight to be administered in single or plural doses as needed to prevent or relieve the arrhythmatic dysfunction. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose, for a 70 kilogram human adult, containing from about 350 milligrams to about 1 gram of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following examples illustrate the preparation of a representative number of compounds of this invention. After each example, the percentage incidence of ventricular fibrillation (VF) after dosing with 10 mg/kg of the exemplified compound is presented for comparison with the control incidence of ventricular fibrillation of 73 percent of animals receiving vehicle alone.

EXAMPLE 1

[5-[3-(Dimethylamino)propyl]-6,7,8,9,10,11-hexahydro-5H-cyclooct[b]-indol-1-yl]carbamic acid 2-(diethylamino)ethyl ester 3-Nitrophenylhydrazine hydrochloride (50 g, 0.26 mol) and cyclooctanone (32.2 g, 0.25 mol) were refluxed in 400 mL of glacial acetic acid for 6 hours. The solution was allowed to cool and the separated solid was filtered, washed with water and recrystallized from aboslute ethanol to afford 20 g (31% yield) of 6,7,8,9,10,11-hexahydro-1-nitro-5H-cyclooct[b]indole; m.p. 189°–191° C.

Analysis for: $C_{14}H_{16}N_2O_2$. Calculated: C, 68.85; H, 6.55; N, 11.47. Found: C, 68.78; H, 6.68; N, 11.43.

The mother liquor was concentrated and diluted with 200 mL of cold water.

The separated solid was filtered, dried and recrystallized from diethyl ether to afford 7 g (11.5% yield) of 6,7,8,9,10,11-hexahydro-3-nitro-5H-cyclooct[b]indole; m.p. 119°–120° C.

Analysis for: $C_{14}H_{16}N_2O_2$. Calculated: C, 68.85; H, 6.55; N, 11.47. Found: C, 68.90; H, 6.64; N, 11.38.

To a stirred mixture of sodium hydride (4.6 g, 0.19 mL) in 60 mL of dry dimethylformamide was added 6,7,8,9,10,11-hexahydro-1-nitro-5H-cyclooct[b]indole (924.4 g, 0.1 mol) over a period of 30 minutes. To this solution was added, while stirring, a solution of N,N-dimethylaminopropyl chloride hydrochloride (15.8 g, 0.1 mol) in 60 mL of dimethylformamide.

The reaction mixture was stirred overnight at 80° C. and dimethylformamide was removed under reduced pressure. The residue was extracted with 3×500 mL of methylene chloride. The methylene chloride extracts were combined, washed with water and dried. Evaporation of the methylene chloride afforded 30 g (90% yield) of 6,7,8,9,10,11-hexahydro-N,N-dimethyl-1-nitro-5H-cyclooct[b]indole-5-propanamine as a red oil. The oil was converted to the hydrochloride salt using diethyl ether/HCl and was recrystallized from ethanol; m.p. 196°–199° C.

Analysis for: $C_{19}H_{27}N_3O_2 \cdot HCl$. Calculated: C, 62.38; H, 7.66; N, 11.49. Found: C, 62.39; H, 7.50; N, 11.25.

6,7,8,9,10,11-Hexahydro-N,N-dimethyl-1-nitro-5H-cyclooct[b]indole-5-propanamine (6 g, 0.01 mol) was dissolved in 50 mL of absolute ethanol. To this solution was added 1 g of 10% Pd/C and the reaction mixture was hydrogenated for 60 minutes (no further hydrogen uptake was observed). The catalyst was filtered and the ethanolic solution was evaporated under reduced pressure.

The product, 1-amino-6,7,8,9,10,11-hexahydro-N,N-dimethyl-5H-cyclooct[b]indole-5-propanamine, as a dark residue, was converted to the dihydrochloride salt; m.p. 202°–206° C.

Analysis for: $C_{19}H_{29}N_3 \cdot 2HCl \cdot 2H_2O$. Calculated: C, 55.88; H, 8.08; N, 10.29. Found: C, 56.03; H, 8.11; N, 10.11.

Trichloromethylchloroformate (1 g, 0.005 mol) was added dropwise to a solution of 1-amino-5H-6,7,8,9,10,11-hexahydro-N,N-dimethyl-cyclooct[b]indole-5-propanamine (2.9 g, 0.01 mol) in 60 mL of dry dioxane. The reaction mixture was stirred at 60° C. for 4 hours and then cooled and dioxane was evaporated under reduced pressure. The resulting residue was dissolved in 70 mL of methylene chloride and to this solution was added, while stirring, N,N-diethylaminoethanol (2.3 g, 0.02 mol) and the reaction was stirred overnight. The methylene chloride was washed with water, dried and evaporated to afford the title compound which was converted to the dihydrochloride salt; m.p. 220°–224° C.

Analysis for: $C_{26}H_{42}N_4O_2.2HCl.H_2O$. Calculted: C, 58.53; H, 8.63; N, 10.50; Cl, 13.22. Found: C, 58.72; H, 8.35; N, 11.19; Cl, 13.51.

VF=20%.

EXAMPLE 2

[5-[3-(Dimethylamino)propyl]-6,7,8,9,10,11-hexahydro-5H-cyclooct[b]indol-2-yl]carbamic acid ethyl ester 6,7,8,9,10,11-Hexahydro-N,N-dimethyl-2-nitro-5H-cyclooct[b]indole-5-propanamine was prepared following the procedure of Example 1, using 6,7,8,9,10,11-hexahydro-2-nitro-5H-cyclooct[b]indole (Rice et al., U.S. Pat. No. 3,282,942) instead of 6,7,8,9,10,11-hexahydro-1-nitro-5H-cyclooct[b]indole and was converted to the hydrochloride salt; m.p. 233°–235° C.

Analysis for: $C_{19}H_{27}N_3O_2.HCl$. Calculated: C, 62.36; H, 7.71; N, 11.47; Cl, 9.69. Found: C, 62.03; H, 7.57; N, 11.17; Cl, 9.75.

2-Amino-6,7,8,9,10,11-hexahydro-N,N-dimethyl-5H-cyclooct[b]indole-5-propanamine was prepared from the 2-nitro product of the preceding paragraph, following the procedure of Example 1 and was converted to the dihydrochloride salt; m.p. 287°–289° C.

Analysis for: $C_{19}H_{29}N_3.2HCl$. Calculated: C, 61.28; H, 8.39; N, 11.28; Cl, 19.04. Found: C, 60.98; H, 8.27; N, 10.97; Cl, 18.84.

To a stirred solution of 2-amino-6,7,8,9,10,11-hexahydro-N,N-dimethyl-5H-cyclooct[b]indole-5-propanamine (5 g, 0.017 mol) in 50 mL of acetonitrile was added 5 mL of triethylamine and 5 mL of ethylchloroformate (5.6 g, 0.05 mol).

The reaction mixture was stirred overnight at room temperature. The solvent was removed and the residue was chromatographed on silica gel (300 g) using 50% methanol/ethylacetate to afford 1.8 g (26% yield) of the title compound as a thick oil which was converted to the hydrochloride salt; m.p. 234°–236° C.

Analysis for: $C_{22}H_{33}N_3O_2.HCl$. Calculated: C, 64.76; H, 8.40; N, 10.30; Cl, 8.69. Found: C, 64.56; H, 8.36; N, 10.24; Cl, 8.82.

VF=25%.

EXAMPLE 3

[5-[3-(Dimethylamino)propyl]-6,7,8,9,10,11-hexahydro-5H-cyclooct[b]indol-2-yl]carbamic acid 2-(diethylamino)ethyl ester The title compound was prepared following the procedure of Example 1, using 2-amino-6,7,8,9,10,11-hexahydro-N,N-dimethyl-5H-cyclooct[b]-indole-5-propanamine instead of 1-amino-6,7,8,9,10,11-hexahydro-N,N-dimethyl-5H-cyclooct[b]indole-5-propanamine and was converted to the dihydrochloride salt; m.p. 188°–191° C.

Analysis for: $C_{26}H_{42}N_4O_2.2HCl.H_2O$. Calculated: C, 58.53; H, 8.63; N, 10.50; Cl, 13.32. Found: C, 58.79; H, 8.76; N, 10.66; Cl, 13.83.

VF=40%.

EXAMPLE 4

[5-[3-(Dimethylamino)propyl]-6,7,8,9,10,11-hexahydro-5H-cyclooct[b]indol-4-yl]carbamic acid ethyl ester A solution of cyclooctanone (35 g) in 200 mL of ethanol was added to a refluxing mixture of 2-nitrophenylhydrazine (43 g) in 600 mL of ethanol.

Refluxing was continued for 5 hours and 200 mL of hot water was added and the mixture was allowed to cool. The cyclooctanone 2-nitrophenyl hydrazone formed appeared as a red oil (62 g) and was used without further purification.

The crude hydrazone (60 g) was refluxed in 600 mL of glacial acetic acid saturated with hydrogen chloride gas for 18 hours. The reaction mixture was allowed to cool and the separated crystals of 6,7,8,9,10,11-hexahydro-4-nitro-5H-cyclooct[b]indole were filtered and dried; m.p. 126°–128° C.

6,7,8,9,10,11-Hexahydro-N,N-dimethyl-4-nitro-5H-cyclooct[b]indole-5-propanamine was prepared following the procedure of Example 1, using 6,7,8,9,10,11-hexahydro-4-nitro-5H-cyclooct[b]indole instead of 6,7,8,9,10,11-hexahydro-1-nitro-5H-cyclooct[b]indole and was converted to the hydrochloride salt; m.p. 174°–176° C.

Analysis for: $C_{19}H_{27}N_3O_2.HCl$. Calculated: C, 62.36; H, 7.71; N, 11.48; Cl, 9.69. Found: C, 62.52; H, 7.75; N, 11.53; Cl, 9.58.

4-amino-6,7,8,9,10,11-hexahydro-N,N-dimethyl-5H-cyclooct[b]indole propanamine was prepared following the procedure of Example 1, using 6,7,8,9,10,11-hexahydro-N,N-dimethyl-4-nitro-5H-cyclooct[b]indole-5-propanamine instead of 6,7,8,9,10,11-hexahydro-N,N-dimethyl-1-nitro-5H-cyclooct[b]indole-5-propanamine and was converted to the dihydrochloride salt; m.p. 276°–278° C.

Analysis for: $C_{19}H_{29}N_3.2HCl$. Calculated: C, 61.28; H, 8.30; N, 11.28; Cl, 19.04. Found: C, 60.92; H, 8.24; N, 11.82; Cl, 18.56.

The title compound was prepared following the procedure of Example 2, using 4-amino-6,7,8,9,10,11-hexahydro-N,N-dimethyl-5H-cyclooct[b]indole-5-propanamine instead of 2-amino-6,7,8,9,10,11-hexahydro-N,N-dimethyl-5H-cyclooct[b]indole-5-propanamine and was converted to the hydrochloride salt; m.p. 192°–194° C.

Analysis for: $C_{22}H_{33}N_2O_2.HCl.\frac{1}{2}H_2O$. Calculated: C, 63.37; H, 8.46; N, 8.46; Cl, 8.50. Found: C, 63.91; H, 8.34; N, 10.47; Cl, 8.66.

VF=40%.

EXAMPLE 5

[5-[3-(Dimethylamino)propyl]-6,7,8,9,10,11-hexahydro-5H-cyclooct[b]indol-3-yl]carbamic acid ethyl ester 6,7,8,9,10,11-Hexahydro-N,N-dimethyl-3-nitro-5H-cyclooct[b]indole-5-propanamine was prepared following the procedure of Example 1, using 6,7,8,9,10,11-hexahydro-3-nitro-5H-cyclooct[b]indole instead of 6,7,8,9,10,11-hexahydro-1-nitro-5H-cyclooct[b]indole and was converted to the hydrochloride salt; m.p. 238°–239° C.

Analysis for: $C_{19}H_{27}N_3O_2.HCl.\frac{1}{2}H_2O$. Calculated: C, 60.88; H, 7.74; N, 11.21; Cl, 9.47. Found: C, 61.26; H, 7.69; N, 11.15; Cl, 9.67.

3-Amino-6,7,8,9,10,11-hexahydro-N,N-dimethyl-5H-cyclooct[b]indole-5-propanamine was prepared following the procedure of Example 1, using 6,7,8,9,10,11-hexahydro-N,N-dimethyl-3-nitro-5H-cyclooct[b]indole-5-propanamine instead of 6,7,8,9,10,11-hexahydro-N,N-dimethyl-1-nitro-5H-cyclooct[b]indole-5-propanamine and was converted to the dihydrochloride salt; m.p. 235°–238° C.

Analysis for: $C_{19}H_{29}N_3.2HCl.2H_2O$. Calculated: C, 55.88; H, 8.08; N, 10.29. Found: C, 56.23; H, 8.34; N, 10.48.

The title compound was prepared following the procedure of Example 2, using 3-amino-6,7,8,9,10,11-hexahydro-N,N-dimethyl-5H-cyclooct[b]indole-5-propanamine instead of 2-amino-6,7,8,9,10,11-hexahydro-N,N-dimethyl-5H-cyclooct[b]indole-5-propanamine and was converted to the hydrochloride salt; m.p. 119°–123° C.

Analysis for: $C_{22}H_{33}N_3O_2.HCl$. Calculated: C, 64.90; H, 8.36; N, 10.30; Cl, 8.73. Found: C, 64.82; H, 8.76; N, 10.09; Cl, 8.94.

VF=40%

EXAMPLE 6

5-[3-(Dimethylamino)propyl]-6,7,8,9,10,11-hexahydro-5H-cyclooct[b]indole-2-carboxylic acid 6,7,8,9,10,11-hexahydro-5H-cyclooct[b]indole-2-carboxylic acid was prepared following the procedure of Example 1, using p-hydrazinobenzoic acid instead of 3-nitrophenylhydrazine; m.p. 240°–241° C.

Analysis for: $C_{15}H_{17}NO_2$. Calculated: C, 74.07; H, 6.99; N, 5.76. Found: C, 73.60; H, 7.11; N, 5.54.

The title compound was prepared following the procedure of Example 1, using 6,7,8,9,10,11-hexahydro-5H-cyclooct[b]indol-2-carboxylic acid instead of 6,7,8,9,10,11-hexahydro-1-nitro-5H-cyclooct[b]indole and was converted to the hydrochloride salt; m.p. 149°–150° C.

Analysis for: $C_{20}H_{28}N_2O_2.HCl.\frac{1}{2}H_2O$. Calculated: C, 64.25; H, 8.03; N, 7.49. Found: C, 63.63; H, 8.09; N, 7.47.

VF=40% and 25% at 15 mg/kg.

EXAMPLE 7

[5-[3(Dimethylamino)propyl]-6,7,8,9,10,11-hexahydro-5H-cyclooct[b]indol-1-yl]carbamic acid, ethyl ester To a solution of 1-amino-5-(3-dimethylaminopropyl)-6,7,8,9,10,11-hexahydro-5H-cyclooct[b]indole (5 g, 0.024 mol) and 5 mL of triethylamine in 80 mL dry acetonitrile (under nitrogen), stirred and kept below 20° C., was added 5 mL ethyl chloroformate. The reaction mixture was stirred at 25°–28° C. for 18 hours. The mixture was diluted with diethyl ether and the precipitate ($Et_3N.HCl$) was filtered off and washed with diethyl ether. The filtrate was dried over sodium sulfate, filtered and the filtrate treated with dry hydrogen chloride. On standing a blueish solid separated. This was filtered, washed with diethyl ether, and dried in a vacuum pistol. There was obtained 1.15 g of the title compound as the hydrochloride.

Analysis for: $C_{22}H_{33}N_3O_2.HCl$. Calculated: C, 64.76; H, 8.40; N, 10.30; Cl, 8.69. Found: C, 63.80; H, 8.43; N, 10.36; Cl, 8.57.

What is claimed is:

1. A method for preventing or relieving cardiac arrhythmia and coronary artery vasospasm which comprises orally or parenterally administering to an aminal in need thereof an effective amount of a compound of the formula:

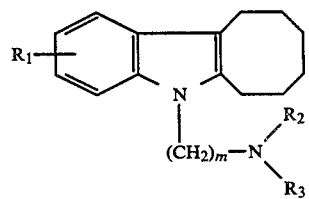

in which
R₁ is —NHCO₂R₈ or —NHCO₂(CH₂)ₒ—NR₉R₁₀
where R₈ is alkyl of 1 to 6 carbon atoms; R₉ and R₁₀ are alkyl of 2 to 6 carbon atoms and o is 1 to 6;
R₂ and R₃ are alkyl of 1 to 6 carbon atoms; and
m is one of the integers 1,2,3 or 4;
or a pharmaceutically acceptable salt thereof.

2. The method of claim 1 in which said compound is [5-[3-(dimethylamino)propyl]-6,7,8,9,10,11-hexahydro-5H-cyclooct[b]indol-1-yl]carbamic acid 2-(diethylamino)ethyl ester or a pharmaceutically acceptable salt thereof.

3. The method of claim 1 in which said compound is [5-[3-(dimethylamino)propyl]-6,7,8,9,10,11-hexahydro-5H-cyclooct[b]indol-2-yl]carbamic acid ethyl ester or a pharmaceutically acceptable salt thereof.

* * * * *